(12) United States Patent
Anderson

(10) Patent No.: US 12,108,957 B2
(45) Date of Patent: Oct. 8, 2024

(54) DEPTH CONTROLLABLE AND MEASURABLE MEDICAL DRIVER DEVICES AND METHODS OF USE

(71) Applicant: Quartus Engineering, Inc., San Diego, CA (US)

(72) Inventor: Wayne Anderson, Las Vegas, NV (US)

(73) Assignee: QUARTUS ENGINEERING, INC., San Diego, CA (US)

( * ) Notice: Subject to any disclaimer, the term of this patent is extended or adjusted under 35 U.S.C. 154(b) by 119 days.

(21) Appl. No.: 18/073,640

(22) Filed: Dec. 2, 2022

(65) Prior Publication Data

US 2023/0165592 A1 Jun. 1, 2023

Related U.S. Application Data

(63) Continuation of application No. 16/667,639, filed on Oct. 29, 2019, now Pat. No. 11,517,324, which is a continuation of application No. 15/389,186, filed on Dec. 22, 2016, now Pat. No. 10,456,146, which is a continuation of application No. 14/473,299, filed on Aug. 29, 2014, now Pat. No. 9,526,511, which is a continuation of application No. 12/474,749, filed on May 29, 2009, now Pat. No. 8,821,493.

(60) Provisional application No. 61/076,105, filed on Jun. 26, 2008.

(51) Int. Cl.
A61B 17/16 (2006.01)
A61B 17/17 (2006.01)
A61B 90/00 (2016.01)

(52) U.S. Cl.
CPC ...... *A61B 17/1624* (2013.01); *A61B 17/1633* (2013.01); *A61B 17/17* (2013.01); *A61B 90/06* (2016.02); *A61B 17/162* (2013.01); *A61B 2090/036* (2016.02); *A61B 2090/062* (2016.02); *A61B 2090/066* (2016.02); *A61B 2217/007* (2013.01)

(58) Field of Classification Search
CPC ........................ A61B 17/1624; A61B 17/1633
See application file for complete search history.

(56) References Cited

U.S. PATENT DOCUMENTS

2009/0093830 A1* 4/2009 Miller ................ A61B 17/1617
606/167
2009/0245956 A1* 10/2009 Apkarian ........... A61B 17/1695
408/11

* cited by examiner

*Primary Examiner* — Olivia C Chang
(74) *Attorney, Agent, or Firm* — Snell & Wilmer, L.L.P.; April Wurster

(57) ABSTRACT

Disclosed are devices and methods for creating a bore in bone. The devices and methods described involve driving a rotating bit in an axial direction such that both rotation and linear movement are controlled and measurable. The instrument is useful for a surgeon to control and simultaneously measure the travel of the tool into the bone and prevent injury to surrounding structures.

17 Claims, 6 Drawing Sheets

DEPTH CONTROLLABLE AND MEASURABLE MEDICAL DRIVER DEVICES AND METHODS OF USE

CROSS REFERENCE TO RELATED APPLICATIONS

This application is a Continuation of U.S. application Ser. No. 16/667,639, filed Oct. 29, 2019, which is a Continuation of U.S. application Ser. No. 15/389,186 filed Dec. 22, 2016, issued on Oct. 29, 2019 as U.S. Pat. No. 10,456,146, which is a continuation of U.S. application Ser. No. 14/473,299 filed Aug. 29, 2014, issued on Dec. 27, 2016 as U.S. Pat. No. 9,526,511, which is a Continuation of U.S. application Ser. No. 12/474,749, filed May 29, 2009, issued on Sep. 2, 2014 as U.S. Pat. No. 8,821,493, which claims the benefit of priority of U.S. Provisional Patent Application Ser. No. 61/076,105, filed Jun. 26, 2008. The filing dates and subject matter of each of the above-noted applications are incorporated by reference in their entireties by reference thereto.

BACKGROUND

Orthopedic surgery can require bone drilling for the repair of fractures or insertion of implants or other devices. The resulting holes are needed to accept screws, implants and other devices to exert pressure, fixation or reduction of the bone. During any procedure where a drill or other driver is used to advance a tool into and through bone, the operator must consciously and carefully limit the penetration to the desired depth. If the operator allows the tool to penetrate further, the patient can suffer injury to distal structures such as nerve, brain, spinal cord, artery, vein, muscle, fascia, bone or joint space structures. These types of injuries can lead to severe patient morbidity and even death. The devices inserted to a drilled bore often must fit within a narrow length range that can vary sometimes by no more than a millimeter or less.

Once the drilling of a bone is safely complete, it is often prudent to obtain the depth of the bore made by the drilling tool. Many procedures require knowledge of the depth of tool penetration, such as in the placement of internal fixation devices, screws and other implantable hardware. Selecting an appropriate length of the screw or other implant necessary for the procedure depends upon such knowledge of the bore's depth. Conventional techniques used in the art are often inconvenient, time consuming and unreliable often requiring trial and error and multiple exposures to radiographs before the proper implant insertion is achieved.

A common way to obtain the depth of the bore formed by a drilling tool is to use a depth gauge. Often surgeons must interrupt the drilling procedure in order to palpate or measure with a depth gauge whether or not the desired depth has been achieved. In many instances a surgeon will take a radiograph during a drilling procedure to confirm the appropriate depth of penetration has been achieved or take a radiograph while the depth gauge is in place to ensure the information the gauge provides is accurate. Depth gauges used in the art can be inaccurate resulting in a surgeon placing a screw of an inappropriate length not often identified until a confirming radiograph is taken. Each radiograph taken increases the radiation exposure of the surgeon, staff and patient in the operating suite. Depth gauges known in the art can also break and require the surgeon to retrieve it from the bore. Inconvenient and inaccurate depth measurement devices and methods known in the art can result in improperly sized screws that must be removed and replaced with new properly sized screws. Wasted hardware, increased disruptions and delays in orthopedic procedures ultimately increase the expense of a procedure as well as exposing the surgeon, staff and the patient to unnecessary radiation. The cost of the additional time, the wasted hardware and the radiation exposure are quite significant.

SUMMARY

All the techniques known in the art to drill holes in bone are technically demanding and require separate measuring steps that interrupt the actual drilling of the bone adding time, cost and need for additional confirming radiographs to complete such procedures. There remains a need for safer, controlled drilling methods and devices. There is also a need for an instrument that simultaneously controls and measures the depth of penetration of the instrument during procedures such as placement of internal fixation devices, screws, and other implantable hardware.

In an embodiment, disclosed is a medical drilling device having a housing including a hand-held portion near a proximal end of the housing; an engagement portion near a distal end of the housing; and an actuator. The device also includes an axial drive shaft extending through a region of the housing between the proximal and distal ends; a first drive element coupled to a region of the axial drive shaft; a rotational drive shaft extending through a region of the housing between the proximal and distal ends; a second drive element coupled to a region of the rotational drive shaft; a coupler interchangeably connected to a working tool and the rotational drive shaft, the coupler extends beyond the engagement portion of the housing; a transducer; and an electronics package. In another embodiment, the medical drilling device further includes a drill guide assembly including a drill guide; a forward surface guide and a rear surface guide. The drill guide surrounds the working tool and a distal region of the forward surface guide couples to the drill guide and a proximal region of the forward surface guide couples to the rear surface guide, and the rear surface guide couples to the axial drive shaft.

Also disclosed are methods for creating a bore in bone. In an embodiment the method includes providing a device comprising a housing having a hand-held portion near a proximal end and an engagement portion near a distal end; an axial drive shaft extending through a region of the housing between the proximal and distal ends; a first drive element coupled to a region of the axial drive shaft; a rotational drive shaft extending through a region of the housing between the proximal and distal ends; a second drive element coupled to a region of the rotational drive shaft; a transducer and an electronics package. The method also includes coupling a distal end of the rotational drive shaft to a working tool that is interchangeably connected to the rotational drive shaft by way of a coupler that can extend beyond the engagement portion of the housing. The method also includes dissecting tissue to create an exposed surface of a bone; contacting the engagement portion of the device to the exposed surface of bone; zeroing the transducer; actuating the second drive element to engage and rotate the rotational drive shaft; actuating the first drive element to engage the axial drive shaft to travel axially; creating a bore in the bone with the working tool; reading a display of metering information provided instantaneously from the transducer, the metering information comprising a measure of depth of the working tool into the bore; and removing the working tool from the bore.

Other features and advantages will be apparent from the following description of various embodiments, which illustrate, by way of example, the principles of the disclosed devices and methods.

DETAILED DESCRIPTION

This disclosure relates to a surgical instrument for preparing a bore in animal tissue. Specifically, the disclosure relates to a surgical instrument that drives a rotating tool in which both rotation and linear, axial movement are controlled and measurable. The instrument has both a rotational drive and an axial drive, each of which are controllable by the surgeon. The instrument is useful for enabling a surgeon to control and simultaneously measure the travel of the tool and prevent injury to surrounding structures. Controlling the rotational speed of the drive can be important to reduce the risk of heating surrounding tissue and bone, for example to the point of causing localized burns. Controlling the axial motion can also be important in the prevention of penetrating injuries, for example, to structures distal of the target such as nerve, brain, spinal cord, artery, vein, muscle, fascia, bone or joint space structures.

Figure 1:
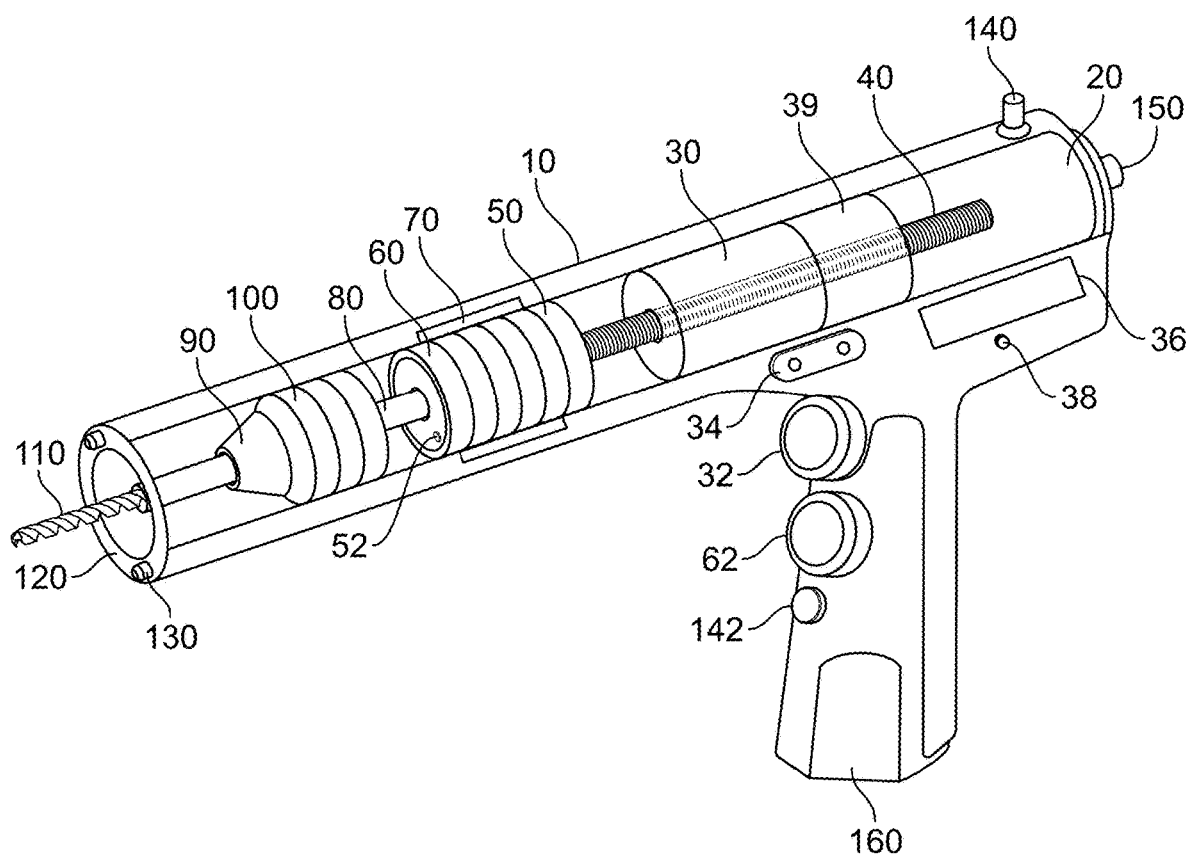
FIG. 1 is a perspective view of one embodiment of a drilling device.

FIG. 1 illustrates a perspective view of one embodiment of an instrument 10. The instrument 10 can include a body 20 that houses a drive shaft 40 and two drive motors 30, 60. Drive motor 30 can be a fixed axial drive motor. Drive motor 30 powers the drive shaft 40, which in turn axially moves the second motor 60. The second drive motor 60 can be a slidable, rotational drive motor. The drive shaft 40 can include a jack screw, ball screw or lead screw and the like. The second drive motor 60 can be fixed against rotational movement and provide for the eventual rotational movement of the working tool 110 located near the distal end of the body 20, described in more detail below. Although the embodiments shown herein use motors, powered by a battery 160, it should be appreciated that other power systems are to be considered, for example pneumatic motors powered by a nitrogen gas source, electrical motors and the like.

The working tool 110 can be, for example a drill bit, Kirshner wire, trochar, burr, reamer, screw driver or other tools. The tool 110 can be made of materials such as titanium metal or stainless steel. A tool made of metal material can be sterilized and reused. Alternatively, the tools 110 can be made of polymeric material that can be discarded after each use. The material can be chosen to provide the necessary strength to allow the proper tool action.

The body 20 of the instrument 10 is shown as a hollow tube having a pistol grip although other configurations are considered herein, for example a straight-bodied instrument. As shown in FIG. 1, the body 20 includes an engagement end 120 near the distal end of the body 20. Proximally the body 20 includes an end piece 150. The end piece 150 can be removed to gain access to the proximal region of the body 20 in order to clean or remove the modular portions of the instrument 10 near the proximal portion such as the drive shaft 40 and the drive motor 30.

A coupler 90 can be housed within the body 20 of the instrument 10 near the distal engagement end 120. The coupler 90 can be rotatably driven and is configured to connect the working tool 110 to the instrument 10. The coupler 90 can be a chuck device such as a common three-jaw chuck in which the jaws grasp the upper portion of the tool 110 and hold it firmly in place. The coupler 90 can be actuated to open or close the jaws by a rotation mechanism or a key or other techniques known in the art. The coupler 90 could also be a quick release type of chuck or coupler.

Figure 2:
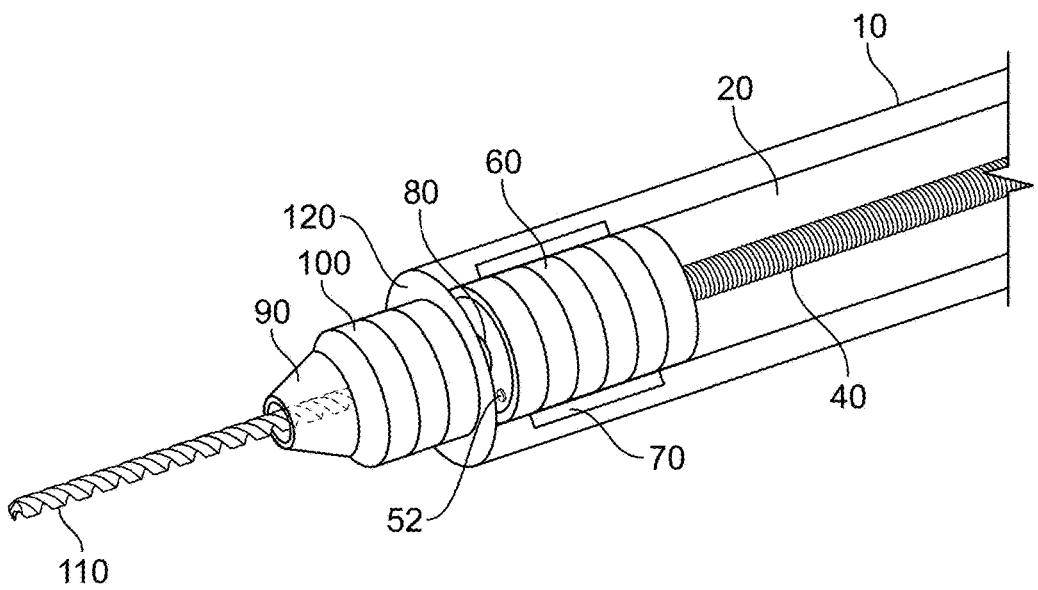
FIG. 2 is a perspective view of the distal end of the embodiment of the device shown in FIG. 1 demonstrating coupler extension.
Figure 4:
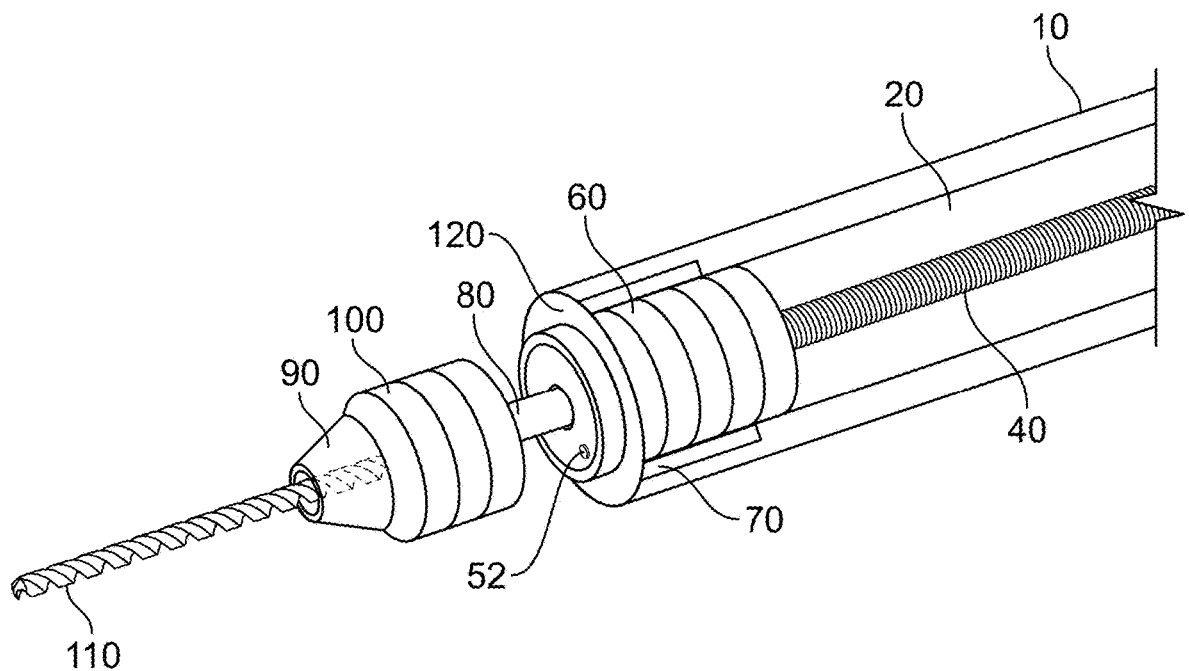
FIG. 4 is a perspective view of the distal end of the device shown in FIG. 2 in which the coupler is extended outside of the body tube.

The coupler 90 can be housed within the body 20 or it can extend beyond the distal engagement end 120 of the body 20 to be accessed external to the body 20 of the instrument 10 (see FIGS. 2 and 4). This accessibility of the coupler 90 externally from the body 20 of the instrument 10 allows for the operator to make reliable connections between the working tool 110 and the coupler 90. The exterior access can also allow for shorter, safer driven tools than if the coupler 90 was internal to the instrument body 20. Additionally, the exterior access can provide for ease of cleaning of this part of the instrument 10.

The drive motor 30 can be housed inside the body 20 and turned on by a drive motor actuator 32. In one embodiment, the drive motor actuator 32 can be a depressible trigger on the handle of the body 20. In an embodiment the speed of the drive motor 30 can be proportional to the degree of actuation of the trigger 32, for example depression of the trigger.

The drive shaft 40 can be a jack screw, ball screw, lead screw and the like and is controlled by the drive motor 30. The drive shaft 40 converts rotary movement of the drive motor 30 to linear movement. The drive shaft 40 can be made to move either in a forward direction or reverse direction that is substantially parallel to the axis of the instrument 10 or tool 110. The direction the drive shaft 40 moves can be determined, for example by the position of a switch 34 changed from the forward or reverse direction.

The drive shaft 40 can translate the torque of the drive motor 30 into thrust of the drive shaft 40. The operator can change the thrust of the drive motor 30, for example, by letting up or pressing down on the trigger 32. The operator can also change the thrust of the instrument by pushing down or letting up on the axial pressure being applied to the instrument. In an embodiment, tissue resistance as compared to axial pressure on the instrument applied by the operator can cause/allow the relative position of the handle of the instrument to feel as if it were backing out of the work as the tool is axially extended from the instrument. This can require the operator to apply additional axial pressure to drive the tool through the tissue. The torque as related to the rotating tool 110 can also change during use of the instrument. This change provides feedback to the operator who in turn can make appropriate adjustments to the axial and rotational movements as needed. In an embodiment, the torque can be changeable, programmable and measurable.

In addition to having control over the speed of rotation, the axial motion of the drive shaft 40 can be controlled and measured. The movement and position of the drive shaft 40 can be measured and displayed such as, for example, by a transducer 39 providing information for display such as by a removable electronics package 36 (described in more detail below). The measurement can be zeroed by the operator prior to use, for example, by depressing the axial measurement selector/reset button 38. This allows the operator to zero the measurement according to the length of the selected tool 110.

The instrument 10 provides the surgeon with instantaneously metered axial motion as the tool 110 penetrates the tissue. The axial motion can be metered by a transducer 39, such as an incremental rotary encoder or absolute rotary encoder (see for example BEI Optical encoder; www.motion-control-info.com/encoder_design_guide.html). The rotation of the jack screw, ball screw or lead screw can be measured and a multiplication performed to determine the distance traveled. This distance can be compared to a set point or zero point. Then, the position of the tool from the distal end of the instrument can be calculated. This calculation relates to depth as determined by the position of the distal end of the instrument with respect to the target tissue (e.g. bone).

In one embodiment, the distal end of the tool 110 is aligned with the distal end of the body 20 and the instrument zeroed. This can be performed manually by the surgeon or electronically with set points and a feedback system (i.e. interface with the coupler). The alignment of the distal end of the tool 110 and the distal end of the body 20 can be such that the two are flush with one another or the distal end of the tool 110 can be some distance beyond the distal end of the body 20, for example 3-7 mm. The tool 110 can be positioned flush against the bone prior to drilling. As the tool 110 advances into the bone, the instrument 10 can be pushed flush against the bone. Alternatively, a drill guide 170 can be used such that the bulk of the instrument is focused into a smaller area of contact, see for example FIG. 3. The drill guide 170 can also fit into a fixation plate for use by the surgeon. The drill guide 170 can fit into the fixation plate by directly pressing or screwing it into one or more of the holes on the fixation plate. The controlled depth medical drilling device can then be connected to the drill guide 170 and the tool 110 aligned with the distal end of the drill guide 170 and fixation plate complex and the instrument zeroed. Once the cut is started and the tool 110 is flush with the bone, the surgeon can use the axial drive to further advance the tool through the bone.

Instantaneous metering of the bore as the tool 110 penetrates the tissue provides an advantage when selecting implants for insertion. For example, the length of the drilling hole and subsequently the length of the implant needed are simultaneously metered upon creating the bore. This eliminates the need for an additional step of measuring with a separate device the depth of the bore created. For example, depth gauges known in the art can frequently provide false measurements. Consequently, surgeons can select the wrong size implant for insertion requiring them to remove it and reinsert a different sized implant. Depth gauges known in the art are also prone to breakage, which can lead to additional time usage and patient morbidity. Controlling and metering the depth of the bore as it is being created prevents repeated trials of implant fixation and eliminates the trial-and-error process of selecting the correct implant for the procedure and improves patient safety. The instrument 10 also saves operating time and the need for additional procedures like repeated radiographs in determining implant size. Because estimates of operating room costs for the personnel alone can be as high as $25 per minute even small savings of time in an operating room can result in large savings of money.

Use of the device and method described herein provides an added benefit of reducing the number of radiographs needed in the operating room. Intra-operative radiographs and radiation exposure are one of the major occupational risks to surgeons and operating room staff. Radiation exposure of this type has been shown to lead to radiation dermatitis, cataracts, skin cancers, leukemia and other cancers. By using a device and method such as that described herein the number of radiographs needed per procedure is reduced as is the life-time exposure of surgeons and staff to x-rays. This reduced radiation exposure ultimately lowers chronic radiation exposure and the risk of radiation-related illnesses in surgeons and their staff.

As mentioned above, the drive motor 60 can be a slidable, rotational drive motor. The drive motor 60 can be housed in the body 20 and connected to the drive shaft 40 by way of a detachable coupler 50. As best shown in FIG. 4, the drive motor 60 can extend up to the distal end of the body 20 and allow for actuation of a release 52 on the coupler 50. When the release 52 is depressed, the operator can disconnect the drive motor 60 from the drive shaft 40 and remove it from the body 20 of the instrument 10. The drive motor 60, drive shaft 80, the coupler 90 and the tool 110 can be modular and can be completely separated from the body 20 of the instrument 10. This allows for interchanging parts as well as cleaning and sterilizing the elements of the instrument 10.

The drive motor 60 can be turned on by actuator 62. In one embodiment, the actuator 62 can be a depressible trigger on the handle of the body 20. In an embodiment the speed of the drive motor 60 can be proportional to the degree of actuation of the trigger 62, for example depression of the trigger. The drive shaft 60 can be a slidable, rotational drive motor that can be made to rotate either in a clockwise or counterclockwise direction as determined by the position of the forward/reverse switch 34, as described above.

In an embodiment, the instrument can include a meter that measures the rotational speed (see for example the speed device described in U.S. Pat. No. 4,723,911), acceleration, deceleration or torque. The meter can provide the surgeon information pertaining to the passage through different layers of tissue. For example, movement of the drill bit through cortical bone into medullary bone, medullary bone to cortical bone, or from cortical bone to soft tissue. The device provides rotation and gradual advancement providing the surgeon with a feel for the type of tissue being passed therethrough, whether it is dense cortical bone or spongier medullary bone.

Figure 5:
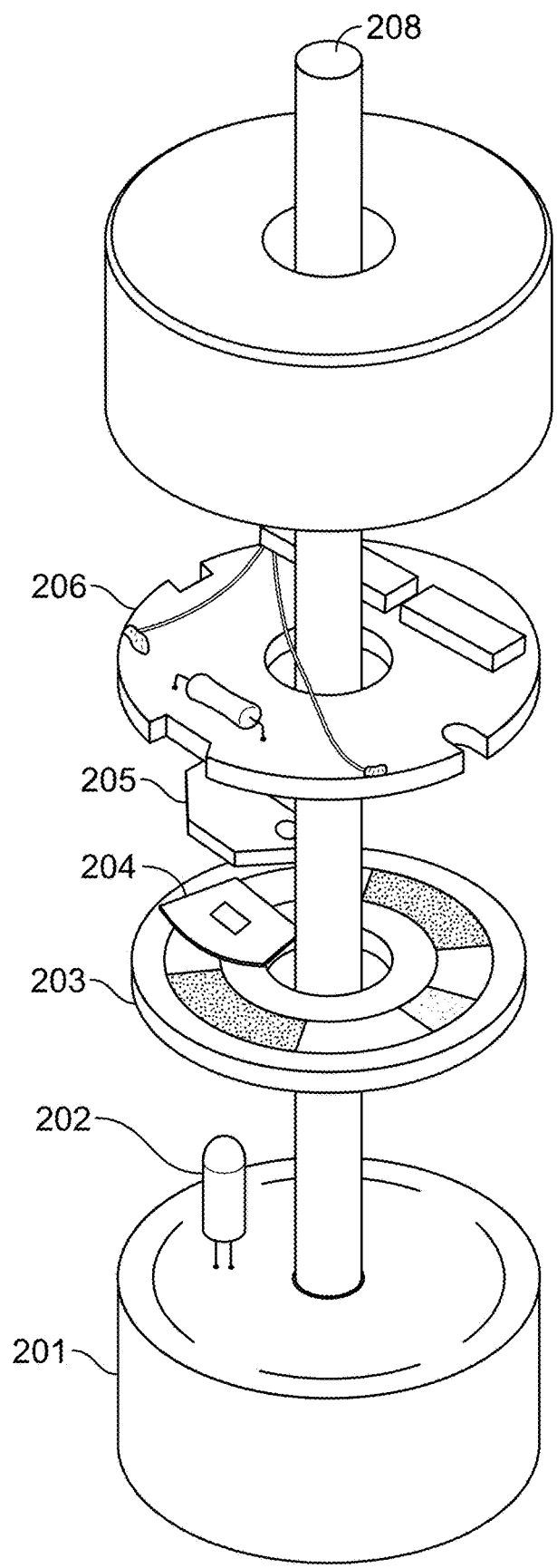
FIG. 5 is a perspective view of an embodiment of a rotary encoder shown in FIG. 1.

In one embodiment, the axial motion can be measured using a transducer or rotary encoder 39. The encoder 30 can measure rotation and convert that information into axial motion. In an embodiment, the rotary encoder 39 includes a bearing housing assembly 201, a light source 202, a code disc 203, a mask 204, a photodetector assembly 205, an electronics board 206 that rotate around shaft 208 (see FIG. 5). In an embodiment, the rotary encoder is an incremental rotary encoder with dual channels in quadrature with an additional data track to provide an internal position reference for setting a "zero point". The rotary encoder 39 can interface with the drive motor 30 and the drive shaft 40. The rotary encoder 39 can provide instantaneous information on the position of the drive shaft 40 regarding the depth of axial movement of the working tool into a bore. This information can be fed to the removable electronics package 36 that can perform count multiplication to determine the tool position.

This rotary encoder 39 can be removable from the body 20 for cleaning and/or repair. The rotary encoder 39 can be mechanical, magnetic, electrical or optical.

In another embodiment, time can be added to the values measured by the rotary encoder. Measuring time can allow for velocity and acceleration to be computed by the removable electronics package 36. The information measured can be displayed by the removable electronics package 36 and provide the surgeon with information pertaining to the passage of the tool through different layers of tissue. For example, movement of the drill bit through cortical bone into medullary bone, medullary bone to cortical bone or from cortical bone to soft tissue. In another embodiment a torque sensor could be applied to the drive motor 60 and provide the surgeon with information pertaining to the passage of the tool through varied layers of tissue.

In addition to automatically measuring depth of penetration during use, the surgeon can control the depth of penetration of the device. In an embodiment, the depth of penetration of the device can incorporate electronics adapted to control the depth of axial movement of the tool 110 into the bore. In an embodiment, the maximum depth of the bore that is to be created by the device can be programmed in advance of drilling with electronics. In an embodiment, the surgeon can feed distally a portion of the working tool 110, for example 30 mm if working on a tibia or femur or 12 mm if working on a radius. The surgeon would then drill through the bone as with an axially static drill. Upon reaching that pre-programmed depth, if the distal cortex had not yet been breached, the axial drive can be used to penetrate the bone further. In another embodiment, the electronics could contain a preset maximum distance that would limit the distal travel of the tool 110. For example, a stop and go signal (i.e. single click of the trigger) or a double stop and go (i.e. double click of the trigger) could release the depth stop and allow further travel. Any of a variety of schedules could be programmed into the electronics to control distal advancement of the tool. For example, using a schedule similar to a snooze alarm system of a typical clock radio could be useful. Each time the tool 110 is advanced after the initial stop the electronics could be programmed to allow only a further distal travel of for example 3 mm or 6 mm or other incremental distance.

Identifying the desired depth of penetration for pre-programmed embodiments can be determined as is known in the art. For example, knowing the age and size of a patient or the typical size of the target tissue from pre-op radiographs and CT scans provide useful information for knowing the desired depth of penetration. A surgeon can also estimate to approximately 70-80%, depending on the bone, that would result in travel through the proximal cortex, the medullar bone and close to or into the distal cortex. Once within the distal cortex, where a great amount of control is needed, the axial drive of the instrument can be used to slowly proceed until a pop is felt or a change in speed can be heard in the drill. This can be augmented by acceleration or torque measurements. For example, as the drill bit penetrates to the very last layers of the distal cortex it can begin to accelerate with a burst of acceleration as it breeches the distal cortex completely, this could also be sensed as a change in torque. The instrument can provide its own auditory output to accentuate the sometimes subtle auditory changes caused by the drill bit. Upon reaching the predetermined target depth, axial movement can slow or stop while rotational movement can continue. The surgeon can override any pre-programmed limitations by actuation/triggers on the device without changing hand positions to continue.

The drive motor 60 can be held rotationally still by the anti-rotation conducting flanges 70. In an embodiment, the flanges 70 slide within channels in the body 20. In an embodiment, each channel can have an opposite polarity such that they conduct electricity from a power source, such as a rechargeable battery 160 in the handle of the body 20, to the drive motor 60. In another embodiment, the power can be separate from the conducting flanges. The anti-rotation conduction flanges can also be spiral shaped and travel through spiral grooves to add stability. The anti-rotation conduction flanges can also be excluded from the device and the rotational drive motor fixed to the axial drive shaft. This would result in the drive motor to turn with the axial drive shaft.

A drive shaft 80 can be connected to and driven by the drive motor 60. The drive shaft 80 can be also connected to the coupler 90 that holds the tool 110. The coupler 90 is stabilized within the body 20 by bearings 100. The bearings 100 can be axially slidable and stabilizing.

In an embodiment, the instrument can include an irrigation system. The irrigation system can include one or more irrigation nozzles 130, an irrigation port 140, and an irrigation actuator 142. The irrigation actuator 142 can be a depressible trigger on the handle of the body 20. The actuator 142 can turn on the flow of irrigation through the nozzles 130 to be delivered to the surgical field. The irrigation nozzles 130 can be located at or near the engagement end 120 of the body 20. The irrigation nozzles 130 can be connected through the irrigation port 140 to a sterile fluid bag and sterile tubing (not shown). The irrigation fluid can be delivered to the irrigation port 140 via a sterile fluid bag and sterile tubing. An external fluid pump or gravity can be used to pressurize the irrigation system. The irrigation system can be kept outside the sterile surgical field except, for example, for the sterile tubing connected to the instrument. Such an arrangement can contribute to the engagement end 120 and the tool 110 remaining relatively free from bulk or other awkward equipment enabling more accurate placement and easy use of the instrument 10 in the surgical field.

The irrigation nozzles 130 allow for the surgical field to be kept cool while the instrument is in use. In one embodiment, the irrigation nozzles 130 spray fluid from the tip of the instrument. In another embodiment, the irrigation nozzles 130 can be routed internally through the tool 110 and sprayed from channels near the distal end of the tool. The irrigation nozzles 130 reduce the risk of tissue damage at the site of use such as bone burning and bone death. The irrigation nozzles 130 also can reduce the risk of hardware failure, the need for re-operation, infection, limb loss and death. The instrument can also include a means for suction at or near the surgical field. Suction means can be applied through the nozzles 130 of the irrigation system or can be applied through additional channels.

Figure 3:
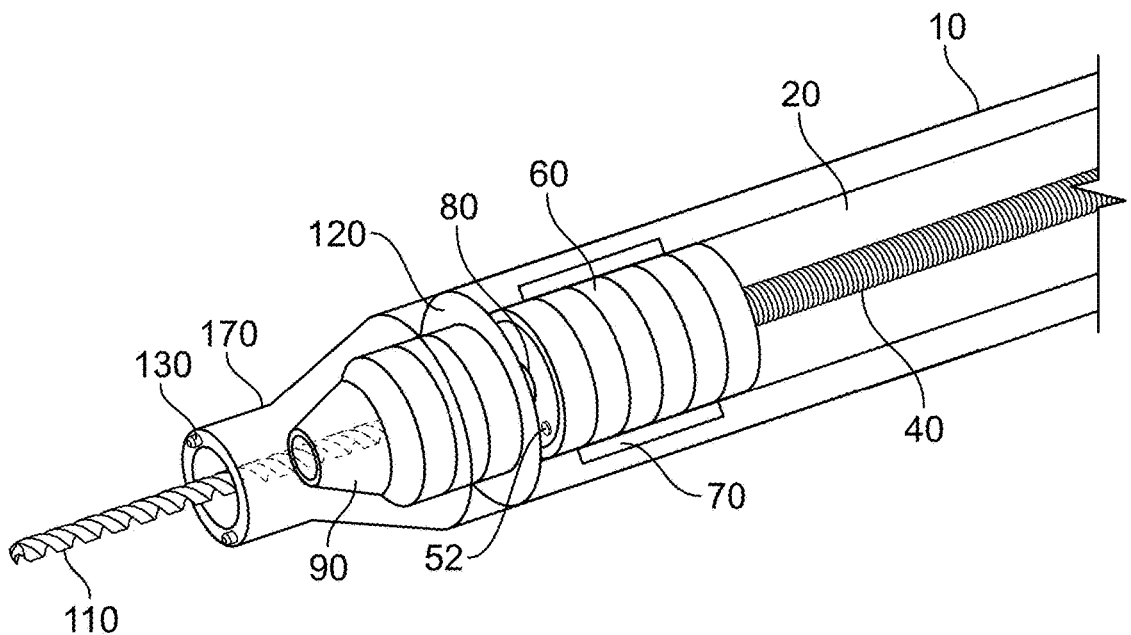
FIG. 3 is a perspective view of the distal end of an embodiment of the device having an attachable/detachable guide with irrigation nozzles.

With respect to FIG. 3, one embodiment of the instrument 10 can include an attachable/detachable guide 170 with or without irrigation nozzles 130. The guide 170 can provide for a smaller diameter at its distal end with which to engage the surgical field compared to the distal end of the body. The electronics package 36 can be zeroed as described above to include the additional axial length of the guide 170.

In use, the drive shaft 40 axially drives the drive motor 60, which rotates the drive shaft 80, which rotates that coupler 90 which rotates the tool 110. The drive shaft 40 is driven in an axial direction by the drive motor 30. In turn, the tool 110 rotates and is also axially translated along the longitudinal axis of the tool. Both the rotational movement and axial displacement of the tool 110 can be controlled in a gradual and steady manner.

Figure 6:
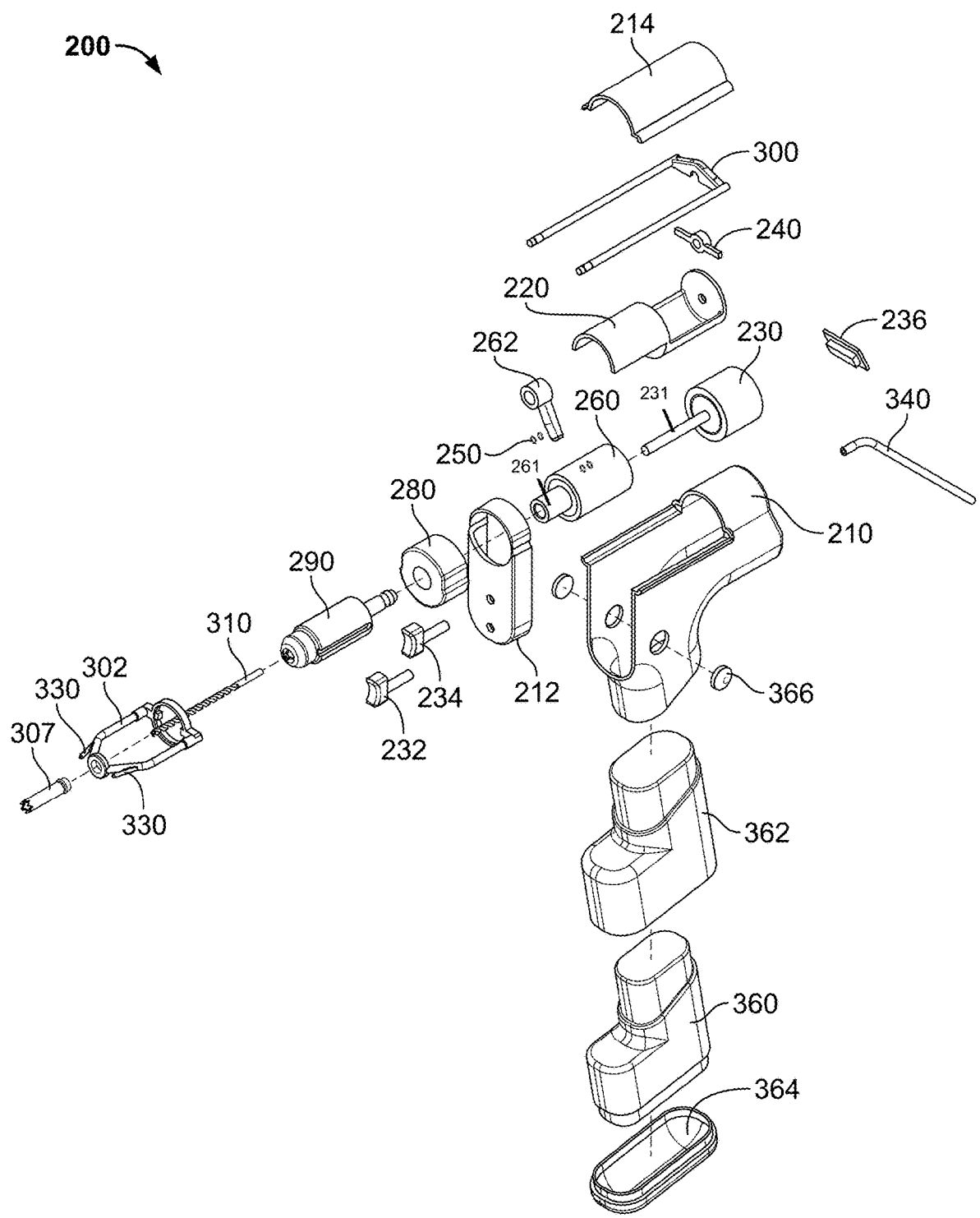
FIG. 6 is a perspective, exploded view of another embodiment of a drilling device.

FIG. 6 illustrates another embodiment of an instrument 200 that allows a surgeon to instantaneously control and measure the depth of the bore. As with the previous embodiments, this embodiment of the device eliminates the extra, unreliable, time-consuming and hazardous steps of using a depth gauge with or without a confirming radiograph. The instrument 200 includes a body 210 that houses two drive motors 230, 260, a rear and forward surface guide 300, 302 and a drill guide 370. Although the embodiments shown herein use motors, it should be appreciated that other power systems are to be considered, for example pneumatic motors powered by a nitrogen gas source, electrical motors and the like.

Drive motor 230 can be an axial drive motor and spindle 231. Drive motor 230 and spindle 231 is seated in the rear of the body 210 and is attached to drive lug 240. The drive motor spindle 231 can function like a jackscrew, a ball screw, a lead screw or the like. The axial drive motor 230 powers the drive lug 240 in an axial direction, which in turn drives the rear surface guide 300, the forward surface guide 302 and the drill guide 370 all in an axial direction.

The second drive motor 260 can be a rotational drive motor and spindle 261. The second drive motor 260 is seated in the front of the body 210. The second drive motor 260 rotationally drives the coupler or chuck 290 and eventually the tool 310. The coupler or chuck 290 can be a chuck device such as a common three-jaw chuck in which the jaws grasp the upper portion of the tool 310 and hold it firmly in place. The coupler or chuck 290 can be actuated to open or close the jaws by a rotation mechanism or a key or other techniques known in the art. The coupler or chuck 290 can be a quick release type of chuck or coupler. The coupler or chuck 290 can connect to a working tool 310. A coupler or chuck extension 280 can also be included.

The working tool 310 can be, for example a drill bit, Kirshner wire, trochar, burr, reamer, screwdriver or other tools. The working tool 310 can be made of materials such as titanium metal or stainless steel. A tool 310 made of metal material can be sterilized and reused or discarded after each use. Alternatively, the tools 310 can be made of polymeric material that can be sterilized and reused or discarded after each use. The material can be chosen to provide the necessary strength to allow the proper tool action. The working tool 310 fits through the distal end of the forward surface guide 302 extending through the drill guide 370 to engage the work.

The depth the tool 310 travels into the work can be measured by a mechanical, magnetic, electrical or optical rotary encoder, or the like. The rotary encoder can be an incremental rotary encoder or an absolute rotary encoder. The depth the tool 310 travels into the work can also be measured by a synchro, a resolver, a rotary variable differential transformer (RVDT) or a rotary potentiometer, or the like. As mentioned above, information regarding use of the instrument can be relayed in real-time to a display 236 with removable electronics package that can be found in the body 210 of the instrument 200 providing instantaneous information such as bore depth during drilling. The display 236 can include an LED or other display using, for example, electrical filaments, plasma, gas or the like.

The rear surface guide 300 attaches to the drive lug 240 at its proximal end and the forward surface guide 302 at its distal end. There can be one or more o-rings 250 between the two surface guides 300, 302. In another embodiment the surface guides 300, 302 can be a single unit. The surface guides 300, 302 shown in the drawings have two "arms" or supports that extend axially. But it should be appreciated that the surface guides 300, 302 can have one, two, three or more arms that provide additional support to bear the load. The forward surface guide 302 can engage the outside of the coupler or chuck 290. In an embodiment the coupler or chuck 290 includes a sleeve and/or stabilizing flanges. In another embodiment, the coupler or chuck 290 can function without a sleeve or stabilizing flanges. In that embodiment the forward surface guide 302 can have a bushing or other device to engage the coupler or chuck 290 directly and still allow the coupler or chuck 290 to spin freely.

The drill guide 370 connects to the distal end of the forward surface guide 302. The drill guide 370 can engage bone, fracture plates or other implants. A drill guide that screws into a fracture plate can provide for directional guidance for the drill bit. The drill guide 370 can be screwed into a fracture plate such that the drill guide 370 can receive a drill bit and can attach to the instrument 200 via the drill guide. The fracture plate can connect to the drill guide 370, the drill guide 370 can connect to the instrument 200 resulting in one interconnected complex for drilling a bore. In one embodiment the drill guide 370 screws into a fracture plate and the instrument 200 can then be attached to the drill guide 370 by connecting the forward surface guide 302 to the drill guide 370.

A body insert 220 can fit inside the top of the body 210 such that it covers the drive motors 230 and 260. The drive lug 240 and the rear surface guide 300 sit in the body 210 above the body insert 220. The top of the body 210 also can accept a body cover 214. The rear surface guide 300 fits between the body 210 and the body cover 214 such that it is free to move within the body 210 and extend beyond the body 210 and the body cover 214. The axial drive motor 230 and spindle 231 and the drive lug 240 determine the movement of the rear surface guide 300. The body 210 also can include a trigger housing 212 having, for example, a forward two-stage trigger 232 and a reverse trigger 234.

In an embodiment the forward two-stage trigger 232 can actuate both drive motors 230, 260. The first stage can engage the rotational drive motor 260. The second stage can engage the axial drive motor 230. The speed of the rotational drive motor 260 can be proportional to the degree of actuation of the first stage of the trigger 232, for example depression of the trigger. The speed of the axial drive motor 230 can be proportional to the degree of actuation of the second stage of the trigger 232. In an embodiment, the further the trigger is pulled while in the first stage and the rotational drive motor 260 is engaged, the faster the tool spins until it is at full speed. The tool spins at full speed just before it enters the second stage and the axial drive motor 230 is engaged and the surface guide begins to move axially.

When the first stage of the two-stage trigger 232 is actuated, the rotational drive motor 260 and spindle 261, the coupler or chuck 290 and the tool 310 spin in a forward direction. When the second stage of the two-stage trigger 232 is actuated, the rotational drive motor 260 and spindle 261, the coupler or chuck 290 and the tool 310 are spinning at maximal speed in a forward direction and the axial drive motor 230 and spindle 231 begins to spin proportional to the degree of actuation of the second stage of the two-stage trigger 232. The action of the axial drive motor 230 and spindle 231 cause the drive lug 240, the rear surface guide 300, the forward surface guide 302 and the drill guide 370 to move in an axial, proximal direction or towards the body 210 of the instrument 200 and away from the target tissue. The axial movement in the proximal direction towards the body 210 of the instrument 200 reveals the tool 310 allowing it to engage with and bore into the work as the operator applies pressure to the instrument 200 and keeps it engaged with the work.

The reverse trigger 234 can cause both of the drive motors 230, 260 to reverse their direction. When the reverse trigger 234 is engaged while the two-stage trigger 232 is actuated during the first stage, the rotational drive motor 260 and spindle 261, the coupler or chuck 290 and the tool 310 spin in a reverse direction. When the second stage of the two-stage trigger 232 is actuated, and the reverse trigger 234 is still engaged, the rotational drive motor 260 and spindle 261, the coupler or chuck 290 and the tool 310 are spinning at maximal speed in a reverse direction and the axial drive motor 230 and spindle 231 begins to spin proportional to the degree of actuation of the second stage of the two-stage trigger 232. The action of the axial drive motor 230 and spindle 231 cause the drive lug 240, the rear surface guide 300, the forward surface guide 302 and the drill guide 370 to move in an axial direction away from the body 210 of the instrument 200. The axial movement away from the body 210 of the instrument 200 pushes the instrument body 210 away from the work and draws the tool 310 out of the work. In another embodiment the motors 230, 260 can have independent reverse functions and can be controlled independently via independent actuators or triggers.

Distal to the trigger housing 212 there can be an oscillation select switch 262. When the oscillation select switch 262 is in the off position, the instrument 200 can function as described above. When the oscillation select switch 262 is in the on position, the rotational drive motor 260 can oscillate in the appropriate direction when the triggers are actuated and the axial drive motor's 230 function is not affected. If the forward trigger is actuated, the instrument 200 oscillates in the forward direction, i.e. the rotational drive motor oscillates forward but the axial drive motor moves smoothly in the forward direction as before. If the reverse and forward triggers are actuated, the instrument 200 oscillates in the reverse direction, i.e. the rotational drive motor oscillates in reverse but the axial drive motor moves smoothly in the reverse direction as before. The oscillation select switch affects the function of the rotational motor not the axial drive motor. When selected it causes the rotational motor to oscillate.

In an embodiment the rotation drive motor 260 can have a torque sensor applied (not shown). When the tool passes cortical bone into medullary bone or from cortical bone into soft tissue the measured torque will drop dramatically. The information can be relayed to the display 236 and integrated with the function of the motor drivers and their actuators. For example, in an embodiment, when the tool 310 is moving axially in a forward direction and passes from cortical bone to medullary bone or from cortical bone to soft tissue the reduced torque will interrupt the axial motion. The axial drive can then be reengaged by releasing pressure on the forward two-stage trigger and reapplying pressure.

The body 210 can accept an irrigation tube 340. Automated irrigation is generally a desired option for surgeons as it effectively reduces drill bit temperature, bone temperature and the risk of bone burning. The forward surface guide 302 can have one or more irrigation nozzles 330. The body 210 can accept an irrigation actuator (not shown), for example a depressible trigger on the handle of the body 210. The irrigation actuator can be part of the electronics package contained in the display 236. The actuator can turn on the flow of irrigation from the irrigation tube 340 through the nozzles 330 to be delivered to the surgical field. The irrigation nozzles 330 can be connected through the irrigation tube 340 to a sterile fluid bag and sterile tubing (not shown). The irrigation fluid can be delivered to the irrigation port 340 via a sterile fluid bag and sterile tubing. An external fluid pump or gravity can be used to pressurize the irrigation system. The irrigation system can be kept outside the sterile surgical field except, for example, for the sterile tubing connected to the instrument. Such an arrangement can contribute to the engagement end and the tool 310 remaining relatively free from bulk or other awkward equipment enabling more accurate placement and easy use of the instrument 200 in the surgical field. In another embodiment the irrigation system can be adapted to supply fluid to the working tool 310 whereas irrigation can travel into the tool 310 and exit through distal ports in the tool 310 and into the work. In another embodiment the irrigation system, or another system of tubes, can be adapted to supply suction to the work area.

The body 210 can accept a battery cover 362 that encloses a battery 360 and is capped on the bottom by a battery case cover 364. The body 210 can accept battery release buttons 366. The body 210 of the instrument 200 together with the battery cover 362, battery case cover 364, body cover 214 and trigger housing 212 is shown as a pistol grip although other configurations are considered herein. For example a straight-bodied instrument or other configuration can be used.

Below is an exemplary method of use for the device or devices described herein. In one embodiment, the surgeon can dissect tissue down to the bone and create a field large enough to put the drill bit or a drill guide or an attachable drill guide against the bone. Screws can be placed across fractures without any other implants or a plate can be fixed across the fracture by bone screws. The screws can lock into the plate and bone. When a plate is to be used, the surgeon can create a field large enough to place the plate. Alternatively, the plate can be inserted through a small incision such that the surgeon slides it along the surface of the bone in combination of blunt dissection of the tissue along the way (i.e. subcutaneous plate). The screws can be placed, for example using a radiograph to find the holes in the plate, through small incisions through the skin with dissection down to the bone. The surrounding tissue can be protected using retractors, a drill guide through which the drill bit is inserted, attachable guides placed on the instrument and the like. If a drill guide is used, the length of the guide is accounted for in the depth measurement. If an attachable guide is used, the depth is automatically or manually zeroed. If a plate is used the thickness of the plate can be automatically or manually accounted for in the zeroing.

The working end of the instrument, with or without a guide, can be placed next to the exposed and dissected bone and the instrument zeroed. Alternatively, the surgeon can extend a few millimeters of the drill bit to engage the bone and drill a counter-sink or pilot hole prior to zeroing the device. Where a fixation plate is used, the plate can be placed next to the bone and the drill end placed snug to the plate. Alternatively, some plates have drill guides that screw into them such that the drill is directed at the proper angle. The instrument disclosed herein can be made such that it attached to or freely engages these types of drill guides. Additionally, drill bit guides can have small spikes to hold their position on the bone. The guide can have spikes to perform this function.

The surgeon then can apply pressure axially and engage first the rotational drive to the desired speed. The surgeon proceeds to engage the axial drive either continuously or incrementally, depending upon the bone density and preference of the user. The drilling can continue through the cortical bone, through the medullary bone, into and through the distal cortical bone. Once through the distal cortical bone as determined by pre-set depth control means, axial resistance, auditory feedback from the rotational speed of the drill and/or auditory feedback from acceleration or torque sensors, the axial movement is stopped. The surgeon can then remove the drill by reversing the axial drive or by pulling back on the instrument. The rotational drive can be left engaged and in the forward direction to facilitate clearing the hole created. The surgeon can then read the depth on the display and select the proper screw for implantation. The screw can be implanted using a manual screw driver or the like.

Figure 7A:
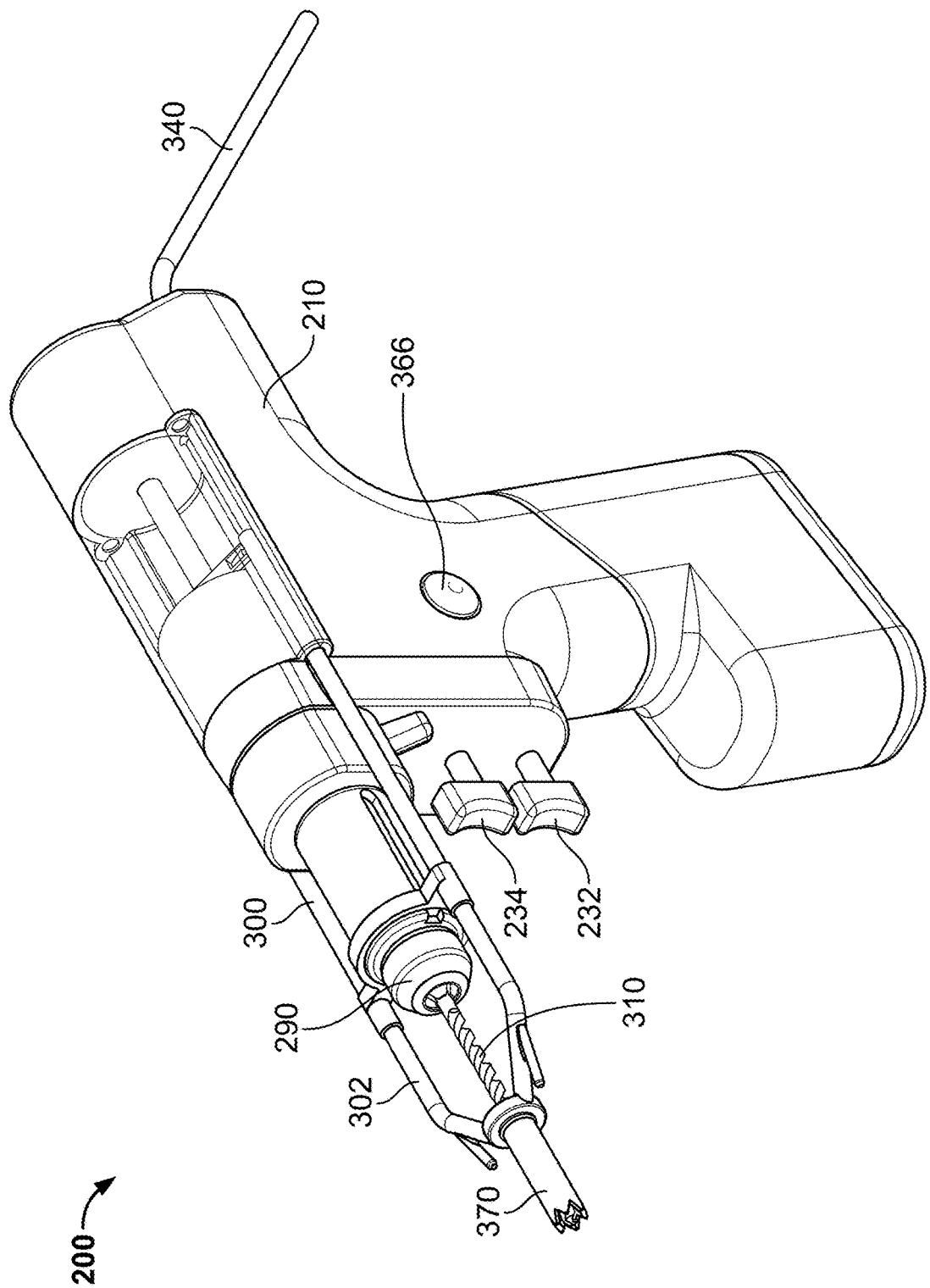
FIGS. 7A-7B are perspective views of the drilling device of FIG. 6.
Figure 7B:
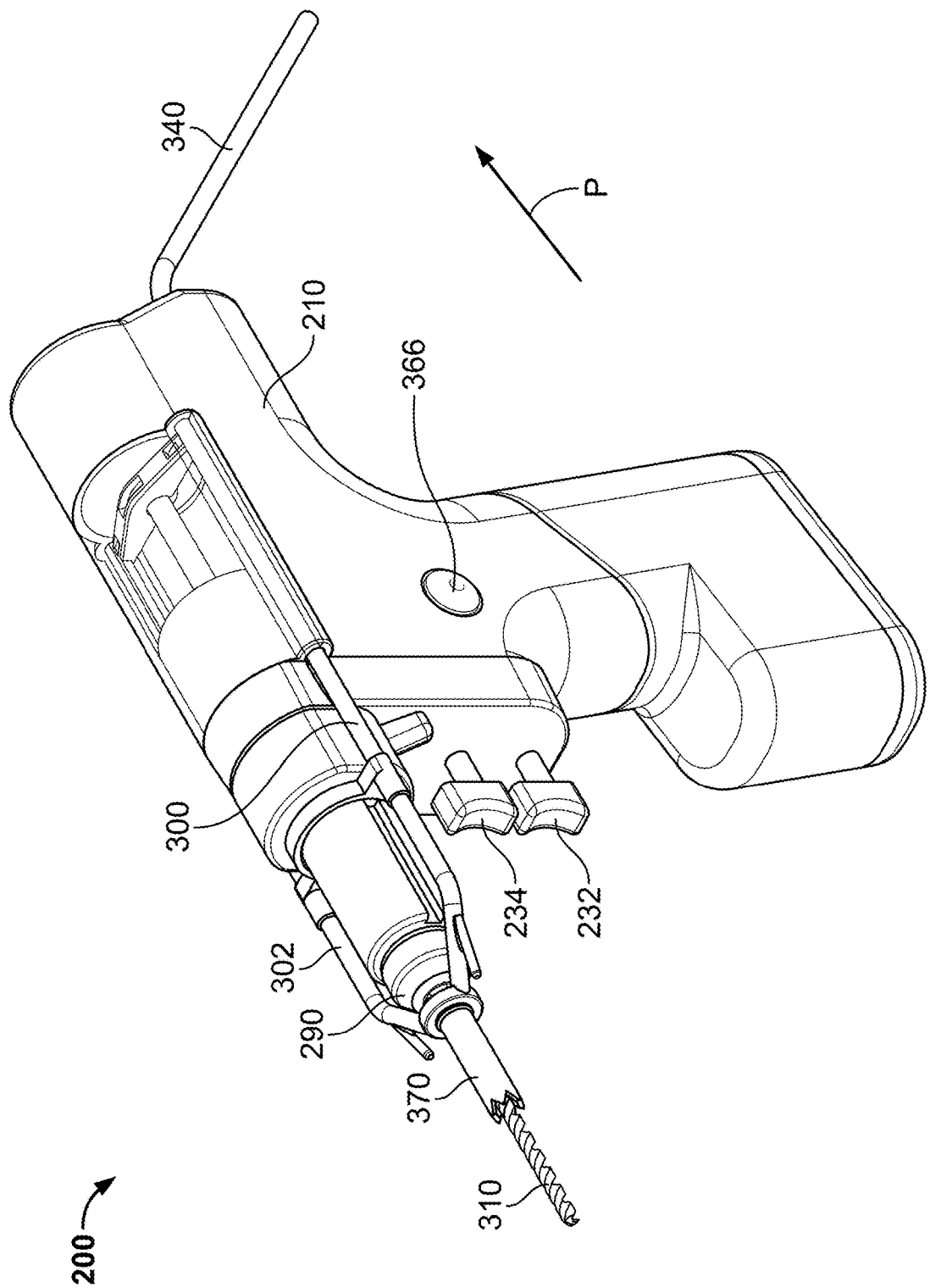

Now with respect to FIGS. 7A-7B, in use the instrument 200 can be set against exposed bone or, if used, the fracture fixation plate. The appropriate zero-depth position can be determined automatically. Once the operator activates the trigger 232, the drill guide 370 retracts in the proximal direction (arrow P) and the working tool 310 extends through the drill guide 370. The working tool 310 engages the work and bores into the work as the operator applies pressure to the instrument 200 and keeps it engaged with the work. The working too 310 can drill into the bone by the amount the drill guide 370 retracts. The drill guide 370 retraction can be measured instantaneously and shown on the display 236 at the back of the instrument 200. The automatic determination of the zero-position whether set against bone or against a fracture fixation plate will depend upon proprietary algorithms related to the way the drill guide 370 sets against the bone or the plate and the thickness of the plate. These variables can be unique to each plating system and set of drill guides. The depth of the travel of working tool 310 into the work is measured and shown on the display 236 simultaneously and instantaneously as the working tool 310 moves axially in a distal direction and penetrates the work.

Once the desired depth of penetration is reached, the reverse trigger 234 can be actuated to cause both of the drive motors 230, 260 to reverse their direction. The action of the axial drive motor 230 causes the drive lug 240, the rear surface guide 300, the forward surface guide 302 and the drill guide 370 to move in an axial direction away from the body 210 of the instrument in a distal direction such that the axial movement pushes the instrument body 210 away from the work and draws the tool 310 out of the work.

While this specification contains many specifics, these should not be construed as limitations on the scope of the claims or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A medical drilling device comprising:
   a housing comprising:
      a hand-held portion;
      an engagement portion; and
      an actuator;
   an axial drive element extending through the housing between a proximal end of the housing and a distal end of the housing;
   a first drive element coupled to the axial drive element;
   a rotational drive element extending through the housing between the proximal and distal ends;
   a second drive element coupled to the rotational drive element;
   a coupler interchangeably connected to a working tool and the rotational drive element, wherein the coupler extends beyond the engagement portion of the housing;
   a first sensor comprising a transducer interfaced to the axial drive element, the transducer configured to measure a depth of the working tool into a bore, the transducer configured to output a first signal representative of advancement of the working tool relative to the distal end of the housing, wherein the first sensor measures a distance of the advancement of the working tool beyond the distal end of the housing; and
   an electronics package in electronic communication with the transducer, the electronics package including a second sensor configured to output a second signal representative of passage of the working tool through layers of tissue having differences in material strength.

2. The device of claim 1, wherein the first drive element comprises a fixed axial drive motor.

3. The device of claim 2, wherein the fixed axial drive motor powers the axial drive element.

4. The device of claim 3, wherein the axial drive element travels a distance in an axial direction.

5. The device of claim 4, wherein the axial drive element travels axially from a proximal to a distal direction or from a distal to a proximal direction relative to the housing.

6. The device of claim 4, wherein the distance the axial drive element travels is instantaneously measured by the transducer.

7. The device of claim 6, wherein the electronics package translates the distance the axial drive element travels within the housing into a depth measurement of axial movement of the working tool into a bone.

8. The device of claim 1, wherein the depth the working tool penetrates a bone is pre-programmed by an operator.

9. The device of claim 1, wherein the axial drive element is selected from the group consisting of a jack screw, a ball screw and a lead screw.

10. The device of claim 1, wherein the second drive element comprises a slidable, rotational drive motor.

11. The device of claim 10, wherein the axial drive element moves the slidable, rotational drive motor in an axial direction.

12. The device of claim 1, wherein the second drive element coupled to the rotational drive element rotates the working tool.

13. The device of claim 1, wherein the working tool is selected from the group consisting of a drill bit, Kirshner wire, trochar, burr, reamer and a screw driver.

14. The device of claim 1, wherein the transducer comprises a rotary encoder.

15. The device of claim 14, wherein the rotary encoder is an incremental rotary encoder or an absolute rotary encoder.

16. The device of claim 15, wherein the rotary encoder is electronic, optical, magnetic or mechanical.

17. The device of claim 1, wherein the working tool defines a distal-most end of the device during an entire range of advancement of the working tool beyond the distal end of the housing.

\* \* \* \* \*